United States Patent [19]

Arold

[11] 4,091,037
[45] May 23, 1978

[54] PREPARATION OF ALKYLTHIOMETHYLPHENOLS

[75] Inventor: Hermann Arold, Wuppertal, Germany

[73] Assignee: Bayer Aktiengesellschaft, Leverkusen, Germany

[21] Appl. No.: 783,370

[22] Filed: Mar. 31, 1977

[30] Foreign Application Priority Data

Apr. 6, 1976 Germany .............................. 2614875

[51] Int. Cl.$^2$ ................. C07C 149/32; C07C 149/34; C07C 149/36
[52] U.S. Cl. ................................................ 260/609 F
[58] Field of Search ..................................... 260/609 F

[56] References Cited

U.S. PATENT DOCUMENTS 2,417,118  3/1947  McCleary et al. ............... 260/609 F

FOREIGN PATENT DOCUMENTS 1,910,588  6/1975  Germany.

OTHER PUBLICATIONS

F. Poppelsdorf et al., J.C.S., 1954, 1124 et seq.
S. Patai, The Chemistry of Carboxylic Acids and Esters, pp. 724–729.

Primary Examiner—Joseph Paul Brust
Assistant Examiner—Molly C. Eakin
Attorney, Agent, or Firm—Burgess, Dinklage & Sprung

[57] ABSTRACT

A process for the preparation of an alkylthiomethylphenol of the formula

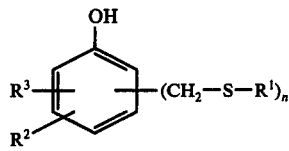

comprising reacting a dialkylaminomethylphenol of the formula

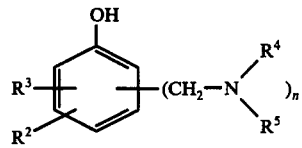

with a thiocarboxylic acid S-ester of the formula

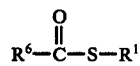

in which
$R^1$ is optionally substituted alkyl with 1 to 12 carbon atoms or optionally substituted phenyl, $R^2$ and $R^3$ each independently is hydrogen, alkyl with 1 to 5 carbon atoms, halogen or nitro, or together form a benzene ring or cycloalkane ring with 3 to 5 carbon atoms which is fused to the phenyl ring,
$R^4$ and $R^5$ each independently is alkyl with 1 to 6 carbon atoms, or together with the nitrogen atom form a five- or six-membered heterocyclic ring,
$R^6$ is hydrogen or alkyl with 1 to 6 carbon atoms, and $n$ is 1, 2 or 3.

The process may be carried out in a solvent, advantageously at a temperature from about 100° to 150° C, at about normal pressure using phenol as a catalyst with about 0.9 to 1.5 moles of thiocarboxylic acid S-ester per mole of dialkylaminomethylphenol.

9 Claims, No Drawings

PREPARATION OF ALKYLTHIOMETHYLPHENOLS

The present invention relates to an unobvious process for the preparation of alkylthiomethylphenols which can be used as intermediates in the synthesis of insecticidally active compounds.

It is known from F. Poppelsdorf, S. J. Holt, J. Chem. Soc. 1954, 1,124 et seq. that aryl- or alkyl-thiomethyl-naphthols can be prepared in a Mannich reaction by reacting, for example, β-naphthol with formaldehyde and an aryl- or alkylmercaptan. However, this process has the disadvantage that reaction times of about 6 days are required in order to obtain satisfactory yields. Furthermore, if this reaction is applied to phenol, a single reaction product is not formed but mixtures of isomers and homologues are obtained.

It is also known from U.S. Pat. No. 2,417,118 that mixtures of alkylthiomethylphenols are obtained by reacting dialkylaminomethylphenols with alkylmercaptans. However, this process has the disadvantage that, because of the high reaction temperatures required, it cannot be applied to low-molecular-weight alkylmercaptans without considerable technical effort (reactions under pressure in an autoclave) and, moreover, mixtures of isomeric and homologous alkylthiomethylphenols are formed in this reaction. A further disadvantage of this procedure is that the required reaction times are 35 to 60 hours and this gives rise to additional losses in yield since the dialkylaminomethylphenols which serve as starting compounds are not stable to heat at the required reaction temperatures and partly resinify during the long reaction time.

The present invention now provides a process for the preparation of an alkylthiomethylphenol of the general formula

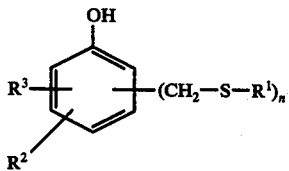

comprising reacting a dialkylaminomethylphenol of the formula

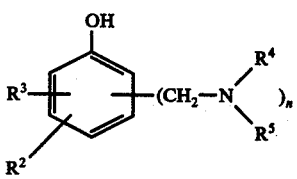

with a thiocarboxylic acid S-ester of the formula

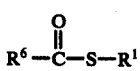

in which
$R^1$ is optionally substituted alkyl with 1 to 12 carbon atoms or optionally substituted phenyl,
$R^2$ and $R^3$ each independently is hydrogen, alkyl with 1 to 5 carbon atoms, halogen or nitro, or together form a benzene ring or cycloalkane ring with 3 to 5 carbon atoms which is fused to the phenyl ring,
$R^4$ and $R^5$ each independently is alkyl with 1 to 6 carbon atoms, or together with the nitrogen atom form a five- or six-membered heterocyclic ring,
$R^6$ is hydrogen or alkyl with 1 to 6 carbon atoms, and
$n$ is 1, 2 or 3.

It is to be regarded as extremely surprising that alkylthiomethylphenols of the formula (I) can be formed in good yields by the process according to the invention, since, according to the state of the art, conversions to the desired products could only be expected in the presence of strong bases and in low yields.

The process according to the invention has a number of advantages. Thus, with the present procedure the reaction can be carried out without excess pressure in every case, even when preparing alkylthio derivatives with 1–4 carbon atoms in the thioalkyl radical, and the reaction proceeds with high space/time yields, even without a diluent. A further advantage is that the reaction can be carried out without the use of additional bases. With the present procedure, no effluents and no gaseous waste products are obtained. The carboxylic acid dialkylamides which are formed in the process as a by-product can be removed by distillation or, after passing in hydrochloric acid gas, precipitated as hydrochlorides and filtered off.

If, for example, o-dimethylaminomethylphenol and thioacetic acid S-ethyl ester are used, the course of the reaction can be represented by the following equation:

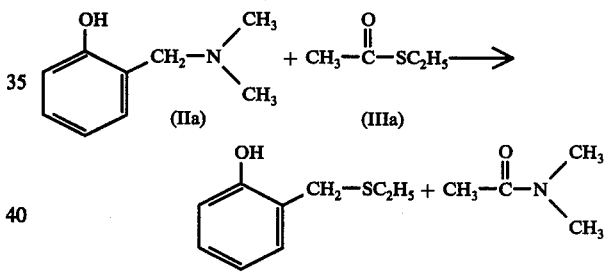

In the above-mentioned formula (II), $R^2$ and $R^3$ preferably denote hydrogen, $C_1$ to $C_4$-alkyl or halogen, especially chlorine, and $R^4$ and $R^5$ preferably denote $C_1$ to $C_4$-alkyl or $C_4$ or $C_5$-cycloalkyl and in the formula (III), $R^1$ preferably denotes $C_1$ to $C_6$-alkyl or alkoxy-substituted alkyl, phenyl, benzyl or $C_1$ to $C_6$-alkyl- and/or halogen-substituted phenyl and $R^6$ preferably denotes $C_1$ to $C_4$-alkyl.

Dialkylaminomethylphenols and thiocarboxylic acid S-alkyl esters which can be used according to the invention as the starting materials are known and can be prepared analogously to known processes.

When carrying out the process according to the invention, 1 mole of dialkylaminomethylphenol is preferably reacted with about 0.5 to 3 moles, and especially with about 0.9 to 1.5 moles, of thiocarboxylic acid S-ester.

The reaction can be carried out at temperatures of 70° to 170° C and preferably at about 100° to 150° C.

The reaction can be carried out without the use of diluents. The use of diluents brings no significant advantages.

The reaction can be carried out without a catalyst, but preferably with about 0.1 to 40% of phenol as the catalyst.

The reaction can be carried out under normal pressure. It is possible to carry out the reaction under elevated pressure but this brings no significant advantages.

The alkylthiomethylphenol formed is isolated by separating it off, by known methods, from the carboxylic acid dialkylamides formed.

The alkylthiomethylphenols which can be prepared by the process according to the invention can be used as intermediates in the synthesis of plant protection agents, especially insecticidally active compounds, such as, for example, 2-ethylthiomethylphenyl N-methylcarbamate according to German Published Specification DOS No. 1,910,588.

The process of the invention will be further described in the following illustrative example:

EXAMPLE

A mixture of 151 g (1 mole) of o-dimethylaminomethylphenol, 108 g (1.04 mole) of thioacetic acid S-ethyl ester and 3 g of phenol was heated to 145° C for 10 hours under normal pressure, while stirring, and then cooled to room temperature.

153 g (91% of theory) of 2-ethylthiomethylphenol could be isolated according to current methods.

The reactions in the table which follows were carried out analogously.

-continued

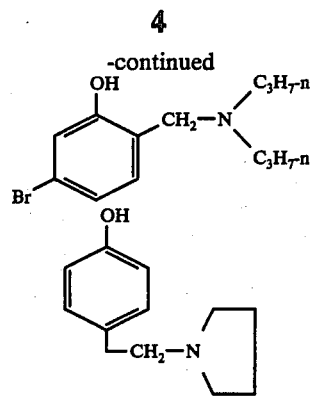

and the like, and other possible representative starting materials (III) include

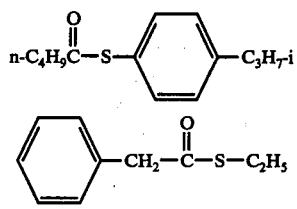

Table $$R^3 \text{—} \underset{R^2}{\text{[phenyl-OH]}} \text{—}(CH_2\text{—}N_{R5}^{R4})_n + R^6\text{—}\underset{\text{O}}{\overset{\|}{C}}\text{—}S\text{—}R^1 \longrightarrow R^3\text{—}\underset{R^2}{\text{[phenyl-OH]}}\text{—}(CH_2\text{—}S\text{—}R_1)_n$$

II                                III                                I

| Compound No. | $R^1$ | $R^2$ | $R^3$ | $R^4$ | $R^5$ | $R^6$ | Position of the dialkyl-aminomethyl group | Amount of starting compound employed II | Amount of starting compound employed III | Catalyst Phenol [g] | Yield of compound (I) in % |
|---|---|---|---|---|---|---|---|---|---|---|---|
| 2 | $CH_3$ | H | H | $CH_3$ | $CH_3$ | $CH_3$ | 2 | 0.5 | 0.53 | 2 | |
| 3 | $C_2H_5$ | H | H | $C_2H_5$ | $C_2H_5$ | $CH_3$ | 2 | 1.0 | 1.04 | 3 | 91 |
| 4 | $C_3H_7$-n | H | H | $C_2H_5$ | $C_2H_5$ | $CH_3$ | 2 | 0.25 | 0.27 | 1 | 88 |
| 5 | $C_4H_9$-n | H | H | $CH_3$ | $CH_3$ | $CH_3$ | 2 | 0.25 | 0.27 | 1 | 90 |
| 6 | Phenyl | H | H | $CH_3$ | $CH_3$ | $CH_3$ | 2 | 0.25 | 0.27 | 1 | 71 |
| 7 | 4-chloro-phenyl | H | H | $C_2H_5$ | $C_2H_5$ | $CH_3$ | 2 | 0.25 | 0.27 | 1 | 85 |
| 8 | $C_2H_5$ | 2-$C_3H_7$-iso | 6-$C_3H_7$-iso | $C_2H_5$ | $C_2H_5$ | $CH_3$ | 4 | 0.5 | 0.53 | 2 | 91 |
| 9 | $C_2H_5$ | 4-Cl | 6-$CH_3$ | $C_2H_5$ | $C_2H_5$ | $CH_3$ | 2 | 0.5 | 0.53 | 2 | 86 |
| 10 | $C_2H_5$ | 4-$CH_3$ | H | $C_2H_5$ | $C_2H_5$ | $CH_3$ | 2 | 0.5 | 0.53 | 2 | 83 |
| 11 | $C_2H_5$ | 4-$NO_2$ | H | $C_2H_5$ | $C_2H_5$ | $CH_3$ | 2 | 0.5 | 0.53 | 2 | 79 |
| 12 | $C_2H_5$ | $C_4H_4$ | | $C_2H_5$ | $C_2H_5$ | $CH_3$ | 2 | 0.5 | 0.53 | 2 | 82 |
| 13 | $C_2H_5$ | H | H | $CH_3$ | $CH_3$ | $C_2H_5$ | 2 | 0.25 | 0.27 | 1 | 78 |
| 14 | $C_2H_5$ | H | H | $CH_3$ | $CH_3$ | $CH_3$ | 2,4 | 0.3 | 0.63 | 1 | 86 |
| 15 | $C_2H_5$ | H | H | $CH_3$ | $CH_3$ | $CH_3$ | 2,6 | 0.3 | 0.63 | 1 | 84 |
| 16 | $C_2H_5$ | H | H | $CH_3$ | $CH_3$ | $CH_3$ | 4 | 0.5 | 0.52 | 2 | 90 |
| 17 | $C_2H_5$ | H | H | $CH_3$ | $CH_3$ | $CH_3$ | 2,4,6 | 0.3 | 1.0 | 1 | 89 |

*)Compound II: 2-diethylaminomethylnaphthol

Other possible representative starting materials (II) include

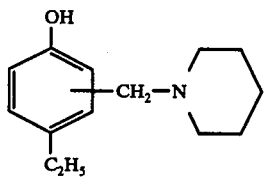

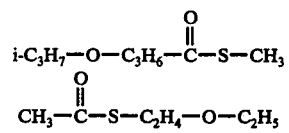

and the like.

It will be appreciated that the instant specification and examples are set forth by way of illustration and not limitation, and that various modifications and changes may be made without departing from the spirit and scope of the present invention.

What is claimed is:

1. A process for the preparation of an alkylthiomethylphenol of the formula

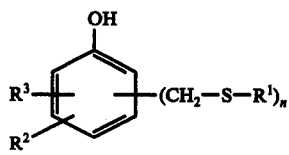

comprising reacting at a temperature of about 70° to 170° C an aminomethylphenol of the formula

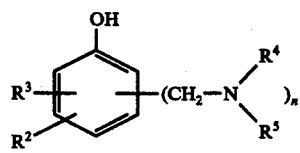

with a thiocarboxylic acid S-ester of the formula

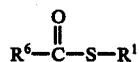

in which
$R^1$ is alkyl with 1 to 12 carbon atoms or alkoxyalkyl with from 1 to 6 carbon atoms in each alkyl moiety, benzyl, phenyl or phenyl carrying at least one $C_{1-6}$ alkyl or halogen substituent,
$R^2$ and $R^3$ each independently is hydrogen, alkyl with 1 to 5 carbon atoms, halogen or nitro, or together form a benzene ring or cycloalkane ring with 3 to 5 carbon atoms which is fused to the phenyl ring,
$R^4$ and $R^5$ each independently is alkyl with 1 to 6 carbon atoms, or together with the nitrogen atom form a five or six-membered heterocyclic ring,
$R_6$ is hydrogen or alkyl with 1 to 6 carbon atoms, and
$n$ is 1, 2 or 3.

2. A process according to claim 1, in which $R^1$ is $C_1$–$C_6$ alkyl, alkoxyalkyl with from 1 to 6 carbon atoms in each alkyl moiety, benzyl, phenyl or phenyl carrying at least one $C_{1-6}$ alkyl or halogen substituent, and $R^2$ and $R^3$ each independently is hydrogen, $C_1$–$C_4$ alkyl or chlorine.

3. A process according to claim 1, in which $R^4$ and $R^5$ each independently is $C_1$–$C_4$ alkyl or together are $C_4H_8$ or $C_5H_{10}$.

4. A process according to claim 1, in which $R^6$ is $C_1$–$C_4$ alkyl.

5. A process according to claim 1, in which the reaction is carried out in the presence of a solvent.

6. A process according to claim 1, in which the reaction is carried out under normal pressure.

7. A process according to claim 1, in which the reaction is carried out using phenol as a catalyst.

8. A process according to claim 1, in which about 0.5 to 3 moles of thiocarboxylic acid S-ester are employed per mole of aminomethylphenol.

9. A process according to claim 2, in which the reaction is carried out at a temperature from about 100° to 150° C, at about normal pressure, using phenol as a catalyst with about 0.9 to 1.5 moles of thiocarboxylic acid S-ester per mole of aminomethylphenol.

* * * * *